(12) United States Patent
Student et al.

(10) Patent No.: US 8,663,665 B2
(45) Date of Patent: *Mar. 4, 2014

(54) ANTI-CHAFING COMPOSITIONS COMPRISING BORON NITRIDE

(75) Inventors: Joerg Student, Stuttgart (DE); Rickson Sun, Palo Alto, CA (US); Kristi Scherler, Akron, OH (US); Paul Hans, Medina, OH (US); Jon Leist, Olmsted, OH (US); Gregory W. Shaffer, Strongsville, OH (US)

(73) Assignee: Momentive Performance Materials Inc., Waterford, NY (US)

( * ) Notice: Subject to any disclaimer, the term of this patent is extended or adjusted under 35 U.S.C. 154(b) by 2091 days.

This patent is subject to a terminal disclaimer.

(21) Appl. No.: 11/554,660

(22) Filed: Oct. 31, 2006

(65) Prior Publication Data

US 2008/0311206 A1    Dec. 18, 2008

Related U.S. Application Data

(60) Provisional application No. 60/778,539, filed on Mar. 2, 2006, provisional application No. 60/807,540, filed on Jul. 17, 2006.

(51) Int. Cl.
*A61K 8/02* (2006.01)
*A61K 9/66* (2006.01)

(52) U.S. Cl.
USPC .......................................... 424/401; 424/455

(58) Field of Classification Search
USPC ......................................................... 424/401
See application file for complete search history.

(56) References Cited

U.S. PATENT DOCUMENTS

| | | | | |
|---|---|---|---|---|
| 5,340,569 A | * | 8/1994 | Elliott et al. | .................... 424/63 |
| 6,124,348 A | | 9/2000 | Wells et al. | |
| 6,645,612 B2 | * | 11/2003 | Pujari et al. | ................... 428/325 |
| 6,824,763 B2 | | 11/2004 | Brooks et al. | |
| 6,951,583 B2 | * | 10/2005 | Clere et al. | ................. 106/287.3 |
| 2007/0207101 A1 | * | 9/2007 | Butts et al. | ....................... 424/63 |

FOREIGN PATENT DOCUMENTS

EP    1055422    11/2000

* cited by examiner

*Primary Examiner* — Layla Soroush
(74) *Attorney, Agent, or Firm* — McDonald Hopkins LLC

(57) ABSTRACT

The invention in one aspect relates to an anti-chafing composition with improved efficacy, in one embodiment, comprising an effective amount of boron nitride suspended in a dermatologically acceptable carrier vehicle. Another embodiment relates to an anti-chafing composition in the form of a powder or a stick containing boron nitride. The present invention also relates to a method of inhibiting or reducing chafing to the skin by topically applying an effective amount of such anti-chafing composition to the skin or to a surface to be in contact with the skin.

13 Claims, No Drawings

ANTI-CHAFING COMPOSITIONS COMPRISING BORON NITRIDE

CROSS-REFERENCE TO RELATED APPLICATIONS

This application claims the benefits of U.S. Patent Appl. Nos. 60/778,539 filed Mar. 2, 2006 and 60/807,540 filed Jul. 17, 2006, which patent application is fully incorporated herein by reference.

FIELD OF THE INVENTION

The present invention relates to anti-chafing compositions for topical applications. The invention also relates to a method to treat and/or prevent chafing to the skin by topically apply a composition comprising boron nitride to a surface in contact with the skin, or to the skin itself.

BACKGROUND OF THE INVENTION

Chafing is skin irritation that occurs where skin rubs against skin, clothing, shoes, or other materials. Chafing sometimes refers to red, sore skin that has been irritated by something rubbing against it. Skin chafing is a problem typically experienced in sports or in the armed services in connection with activities such as running, jogging, hiking, etc. The U.S. Army has contracted with companies to develop and provide special apparel with low friction fiber technology to integrate into various components of the soldier's uniform, for the sole purpose of reducing blisters caused by chafing of the skin. Skin chafing is also a problem in infants in the form of "diaper rash." "Diaper rash" has been defined by the U.S. Food and Drug Administration as an inflammatory skin condition in the diaper area (perineum, buttocks, lower abdomen, and inner thighs) caused by factors including chafing or mechanical (21 CFR §347.3 (1990)).

Solutions to the chafing problem in the prior art range from applications of petroleum jelly or talcum powder as a lubricant on the affected areas of the skin to temporarily alleviate the irritation, or wearing apparel, such as spandex and nylon, to keep body parts from rubbing together, resulting in chafing. Special formulations have been developed such as BODYGLIDE™ skin formulae, containing plant-derived triglycerides or waxes, for topical application on the skin. The application of formulae such as petroleum jelly, plant-derived waxes, or beeswaxes, etc. may create problems in some individuals when the formulae results in blocked skin pores or a greasy or messy residue.

Boron nitride is a ceramic material with unique properties including lubricity, high thermal conductivity, low wear, and low thermal expansion. It has been used in a wide variety of applications, ranging from industrial applications such as thermal spray coatings, thermal management greases, metallization boats, etc., to "high-tech" applications such as neutron detectors in homeland security systems.

Boron nitride has been used in some cosmetic applications such as lipsticks, foundations, and face powders, where softness, lubricity, and opacity properties are desired. It has also been disclosed for topical applications such as body powder. European Patent Publication No. EP 1055422 discloses the use of boron nitride ("BN") in a cosmetic or dermatological formulation, which includes iron-titanium mixed oxide particles, to improve the skin feel and protect the skin from the effects of light, particularly sunlight. BN, in this dermatological formulation, improves the light protective effect of the mixed oxide particles as the bare skin is exposed to sunlight. U.S. Pat. No. 6,824,763 discloses a body powder, which includes a topical anti-fungal agent in combination with at least two excipients, with a boron nitride particulate material coated with a silicone compound as one of the two excipients.

There is still a need for solutions to the skin chafing problem. Applicants have found that boron nitride, with its unique lubricity and thermal conductivity properties, can be used in an anti-chafing composition to minimize skin irritation problems when the skin is in contact with itself or with another surface, and can provide relief and comfort to the wearer.

SUMMARY OF THE INVENTION

In one aspect of the invention, a method for reducing chafing to human skin, comprising topically applying to the human skin a chafing-reducing effective amount of a composition, comprising a dermatologically acceptable anhydrous carrier vehicle, wherein the composition, upon topical application onto the skin, leaves a layer on the skin comprising boron nitride particles.

In a second aspect of the invention, an anti-chafing composition comprises a dermatologically acceptable anhydrous carrier vehicle having suspended therein, wherein the composition, upon topical application onto skin, leaves a layer, comprising a chafing-reducing effective amount of boron nitride particles.

DESCRIPTION OF THE INVENTION

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

As used herein, the term "anti-chafing composition" means any composition capable of reducing, relieving, or minimizing the irritation of skin resulting from the rubbing of skin against skin, clothing, shoes, or other materials.

The term "safe and effective amount," as used herein, means an amount of a compound, component, or composition sufficient to significantly induce a positive benefit, i.e., a comfort feeling or a relief from skin irritation to the wearer, but low enough to avoid serious side effects, i.e. to provide a reasonable benefit to risk ratio, within the scope of sound medical judgement.

The term "suitable adherence to the skin" or "suitably adheres to the skin" means that the anti-chafing composition, after being applied to the skin, remains adhered to the skin long enough, under normal conditions of use, to have an efficacious effect (for example, for treating diaper rash). A layer of composition on the skin may be thought of as a stack of parallel thin layers, each layer being at least one molecule thick. With a composition that has suitable adherence to the skin, the composition's molecular layer closest to the skin (the bottom molecular layer) will temporarily bond physically and/or chemically to the skin on a molecular level, the composition's molecular layer above the bottom molecular layer will temporarily bond physically and/or chemically to that bottom molecular layer, and so on. The bonds between the skin and the bottom molecular layer and between the successive molecular layers cannot be permanent, or else it would be difficult to remove the composition from the skin.

The term "low residue" as used herein refers generally to the residue left on the applied areas of the skin or a surface during or immediately after application of the anti-chafing composition, and is used herein as a measure to help define the composition of the present invention. In this context, low residue measures the L-value, which is determined in accordance with the methodology described hereinafter.

All percentages and ratios used herein are by weight of the total composition and all measurements made are at 25° C., unless otherwise designated. Unless otherwise indicated, all percentages, ratios, and levels of ingredients referred to herein are based on the actual amount of the ingredient, and do not include solvents, fillers, or other materials which may be combined with the ingredient in commercially-available products.

The anti-chafing compositions, according to the disclosure intended for topical application on the skin, may be in the form of a lotion, cream, or fluid gel distributed as an aerosol spray, as a pump-dispenser bottle or an atomizing spray dispenser; a roll-on; a thick cream distributed in a tube; a solid wand (stick); a bar; a water-disintegratable polymeric foam; an icy or hot application; powder applied to an adhesive strip, with the adhesive side against clothing or other material, and the powder side against the skin; or a powder form. In one embodiment, the composition is applied or sprayed onto a sheet or other fabric/apparel for subsequent contact with the skin that requires anti-chafing protection.

The anti-chafing compositions may comprise ingredients generally used in products of this type and well-known to those skilled in the art, provided that they do not interfere with the boron nitride as the anti-chafing active ingredient described herein. The ingredients useful herein may be categorized or described herein by their benefit or their postulated mode of action. However, it is to be understood that the active and other ingredients useful herein can, in some instances, provide more than one therapeutic benefit or operate via more than one mode of action. Therefore, classifications herein are made for the sake of convenience and are not intended to limit an ingredient to the particularly-stated application or applications listed.

Anti-Chafing Ingredient—Boron Nitride:

Boron nitrides, which can be in the anti-chafing composition of the invention, are commercially available from a number of sources, including but not limited to BN powder from GE Advanced Materials, Sintec Keramik, Kawasaki Chemicals, and St. Gobain Ceramics.

In one embodiment, the boron nitride is surface-treated ("coated") to further impart water repellent characteristics to the ingredient. Examples of surface coating materials for the boron nitride powder include, but are not limited to, avocado oil; isohexadecane; liquid paraffin; dimethylpolysiloxane (or dimethicone); a mixture of completely methylated, linear siloxane polymers which have been terminally blocked with trimethylsiloxy units; a silazane compound possessing perfluoroalkyl groups; a zirconate coupling agent; a zirconium aluminate coupling agent; an aluminate coupling agent; and mixtures thereof.

In one embodiment, the boron nitride powder particles have an average particle size of less than 250 µm. In a second embodiment, less than 50 µm. In a third embodiment, in the range of 10 to 30 µm. In a fourth embodiment, having an average particle size of less than 20 µm.

The total amount of boron nitride in the finished dermatological anti-chafing formulation may be varied within wide parameters, but should be such an amount for the composition to have a coating layer on the applied surface for the layer to suitably adheres to the skin to effectively inhibit or reduce irritation or chafing to the skin, and/or effectively reduce damage to the skin by rubbing against another object such as apparel. This amount is a chafe-reducing effective amount, which provides a therapeutic and/or protective skin benefit upon contact with and/or transfer to the skin. Generally, in one embodiment, the chafe-reducing effective amount is in the range of 0.5 to 99.9 wt. %, based on the total weight of the formulation. In a second embodiment, the amount ranges from 1 wt. % to 60 wt. %. In a third embodiment, from 5 wt. % to 40 wt. %. In a fourth embodiment, the amount ranges from 5 to 30 wt. %. In a fifth embodiment, this amount is between 2 to 15 wt. %. In a sixth embodiment, the amount of BN is 40-95 wt. %.

In one embodiment, the BN anti-chafing composition is applied in the pure BN powder form (i.e., consisting essentially of BN in an amount of 90-99.9 wt. %), and the composition comprises agglomerates of hBN platelets, with an agglomerate size distribution of about 10 to about 125 µm. In one embodiment, the boron nitride powder particles have a primary average particle size of less than 250 µm. In a second embodiment, the primary average particle size is less than 50 µm. In a third embodiment, in the range of 10 to 30 µm. In a fourth embodiment, having a primary average particle size of less than 20 µm. In one embodiment, the anti-chafing powder composition consists essentially of hBN platelets having an aspect ratio of about 10 to about 300. In a third embodiment, the anti-chafing powder composition consists essentially of hBN particles having an oxygen content from 0.2 to 2.5 wt %. In a fourth embodiment, the anti-chafing powder composition consists essentially of hBN particles having a graphitization index of less than 7.

For embodiments wherein the boron nitride component is used in a form other than pure BN powder, i.e., in a form with a carrier ingredient as a cream, a lotion, a liquid, etc., the anti-chafing composition may also comprise at least one adjuvant chosen from waxes, softeners, antioxidants, opacifiers, stabilizers, moisturizers, vitamins, fragrances, bactericides, preserving agents, polymers, fragrances, thickeners, propellants, or any other ingredient usually used for this type of topical/dermatological application. A description of exemplary embodiments and ingredients follows.

Carrier Vehicle/Surfactant for the Anti-Chafing Composition:

In one embodiment, the anti-chafing composition is anhydrous. As used herein, "anhydrous" means a composition whose content is free of or having an added water level of less than 3%. In one embodiment, the content of added water is less than 1%, by weight relative to the total weight of the composition. In second embodiment, the anti-chafing composition comprises a blend of liquid carrier and surfactant.

Examples of surfactants include anionic, nonionic, and amphoteric surfactants, as long as they do not adversely interact with the ingredients used in the anti-chafing composition, nor in any way that may be irritating to the skin. Examples of nonionic surfactants include alkoxylated $C_{11}$-$C_{22}$ fatty alkyl hydrophobes. Examples of anionics and amphoterics include betaines. In one embodiment, nonionic surfactants are used to induce gelation, thus hardening the composition if applied in the form of a stick.

In one embodiment, the anti-chafing composition comprises at least one aqueous phase formulated, for example, in a form chosen from aqueous lotions, water-in-oil emulsions, oil-in-water emulsions, and multiple emulsions, e.g., oil-in-water-in-oil and water-in-oil-in-water triple emulsions (such emulsions are known and described, for example, by C. F. Fox in "Cosmetics and Toiletries", November 1986, Vol. 101, pages 101-112). In one embodiment, the at least one aqueous phase comprises water and generally other water-soluble or water-miscible solvents. The water-soluble or water-miscible solvents may be chosen from short-chain monoalcohols, for example, monoalcohols of $C_1$-$C_4$, such as ethanol and isopropanol; and diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. In one embodiment, the carrier vehicle comprises propylene glycol and/or glycerol.

In one embodiment, the composition comprises at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20-25° C.).

In one embodiment, the at least one water-immiscible organic liquid phase is chosen from an oil and a mixture of oils and comprises at least 80% of compounds with a vapor pressure not exceeding 4 kPa (30 mmHg) at 25° C. The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463.

As used herein, volatile silicones are defined, in a known manner, as being compounds that are volatile at room temperature. Mention may be made, for example, among these compounds, to cyclic and linear volatile silicones of the dimethylsiloxane type, whose chains comprise from 3 to 9 silicone-based residues. Cyclomethicones $D_4$, $D_5$ and $D_6$ may, for example, be used. As used herein, non-volatile silicones are defined, in a known manner, as being compounds with a low vapor pressure at room temperature, such as polyalkylsiloxanes, such as linear polyalkylsiloxanes, including linear polydimethylsiloxanes, or dimethicones; polyalkylarylsiloxanes, for example, polymethylphenylsiloxanes; and copolymers of polyether and siloxane, for example, dimethicone copolyols.

Among the non-volatile emollient oils that may be used, examples include hydrocarbon-based derivatives, mineral oils, fatty alcohols, esters of $C_3$-$C_{18}$ alcohols with $C_3$-$C_{18}$ acids, esters of benzoic acid with $C_{12}$-$C_{18}$ alcohols and mixtures thereof, $C_2$-$C_6$ polyols, for example, chosen from glycerol, propylene glycol or sorbitol, polyalkylene glycol polymers. In one embodiment, the emollient oil is present in an amount ranging from 1% to 50 wt. % of the composition. In a second embodiment, from 5% to 40 wt. %.

Other suitable liquid carriers include organic solvents. Suitable organic solvents have a melting point of less than 10° C., which benefit both low temperature storage stability and ease of manufacture. Examples include aliphatic alcohols (monohydric or polyhydric, preferably having 2 to 8 carbon atoms) and polyglycol ethers such as dipropylene glycol, glycerol propylene glycol, butylene glycol, ethanol, propanol, isopropanol, and industrial methylated spirits. Examples of organic solvents include aliphatic alcohols, such as ethanol and isopropanol. In one embodiment, the liquid carriers comprise at least one of a salicylate-based compound, such as glycol salicylate and methyl salicylate, acetone, and menthol, for an icy cold sensation upon application.

Mixtures of carrier materials and/or surfactants are also usable. The total amount of carrier material employed is for some embodiments, from 30% to 99%, and for other embodiments, from 60% to 98%, expressed as a weight percentage of the total weight of the composition.

Structural/Filler Components:

In one embodiment, the anti-chafing composition further includes at least one other agent that imparts structure to the composition, or for gelling, at least one water-immiscible organic liquid phase of the composition, including organic structurants that are non-polymeric or polymeric. Examples of non-polymeric structurants include, but are not limited to, waxes and gellants, such as fatty acids or salts thereof, often containing from 12 to 30 carbons, such as stearic acid or sodium stearate, and/or fatty alcohols (typically insoluble in water), often containing from 12 to 30 carbons; elastomeric polyorganosiloxanes such as those described in International Patent Application No. WO 97/44010.

The term "fatty," as used herein, refers to a long chain aliphatic group, such as at least 8 to 12 linear carbons, which is frequently not branched (linear) and is typically saturated, but which can alternatively be branched and/or unsaturated. It is possible for the fatty acid to contain a hydroxyl group, as in 12-hydroxystearic acid, for example, as part of a gellant combination, and to employ amino or ester derivatives thereof. Examples of suitable higher molecular weight alcohols include behenyl alcohol and sterols such as lanosterol.

The waxes may be chosen from animal, fossil, plant, mineral, and synthetic waxes. Mention may be made, for example, to beeswaxes, carnauba wax, candelilla wax, sugar cane wax, Japan wax, ozokerites, montan wax, microcrystalline waxes, paraffins, and silicone waxes and resins. The thickeners, which are, for example, non-ionic, may be chosen from modified and unmodified guar gums and celluloses, such as hydroxypropyl guar gum and cetylhydroxyethylcellulose.

In one embodiment, the anti-chafing composition further comprises stabilizers selected from particulate organic or inorganic materials, which are dispersible or dissolvable in the formulation. Examples include silica, mineral pigments, organic pigments, crosslinked polymers and copolymers of acrylic acid, cellulose ethers, and mixtures thereof. Examples of mineral pigments include, but are not limited to, calcium carbonate, titanium dioxide, clay, organophilic clay, talc, and gypsum.

In one embodiment, the stabilizer is in the form of a filler material selected from polyamide particles; polyethylene powders; microspheres based on acrylic copolymers, such as those made of ethylene glycol dimethacrylate/lauryl methacrylate copolymer; polymethyl methacrylate microspheres; ethylene-acrylate copolymer powders; expanded powders such as hollow microspheres and, for example, microspheres formed from a terpolymer of vinylidene chloride, of acrylonitrile, and of methacrylate; powders of natural organic materials such as starch powders; silicone resin microbeads; amino acid powders such as lauroyllysine powder; and mixtures thereof.

In one embodiment, wherein the anti-chafing composition is in the form of a liquid stick, a cellulose ether, such as carboxymethyl cellulose and hydroxypropyl cellulose, is added as a structurant in concentrations of up to 1.0%. In another embodiment, wherein structural components such as dibenzylidene sorbitol (DBS) are used, the composition may further comprise an amino acid salt in an amount effective to stabilize the DBS. In yet another embodiment, the composition comprises a solid triglyceride gellant as a structurant.

In one embodiment, the anti-chafing composition uses stearyl alcohol as a structural component in an amount of up to about 15% by weight.

In one embodiment, the anti-chafing composition is in the form of water-disintegratable, polymeric foam that provides topical delivery of the anti-chafing ingredients to the skin, while only slowly disintegrating and rinsing away with water during prolonged single-use or other similar application. In this embodiment, a surfactant paste containing the anti-chafing ingredients, is applied onto a disintegrated polymeric foam as disclosed in U.S. Patent Publication No. 20030180242A1, having a foam thickness of about 0.2 mm to about 40 mm. The polymeric foam contains a structural component having a viscosity of less than about 15 cP, in accordance with a Cold Water Insolubility Test, and a viscosity of greater than about 10 cP, in accordance with a Hot Water Solubility Test, selected from the group consisting of polyvinyl alcohols, polyvinyl pyrrolidone, polyalkylene oxides, celluloses, cellulose derivatives, polysaccharides, polysaccharide derivatives, polycarboxylic acids, salts of polycarboxylic acids, polyamino acids, peptides, polyamides, polyacrylamides, polyesters, poly (vinyl methyl ether-co-maleic anhydride), alginates, alginate derivatives, pectins, polyethylene oxides, gelatins, carrageenans, chitosans, starches, starch derivatives, and combinations thereof.

Optional Components:

The composition of the invention also can comprise other components that may be chosen depending on the carrier and/or the intended use of the formulation. The optional components are used in an amount that does not substantially, adversely impact the anti-chafing effect.

In one embodiment, the anti-chafing composition further comprises a cosmetic or pharmacological component which functions as liquid carrier, as well as to provide soothing comfort to the body, e.g., a salicylate-based compound such as glycol salicylate and methyl salicylate, menthol, and mixtures thereof.

Propellant Component:

In one embodiment, wherein the anti-chafing composition is used as an aerosol application, the composition is used in a container/device, which further contains at least one propellant for distributing the aerosol composition.

Examples of the propellants that are generally used with the anti-chafing product of this type, include but are not limited to, dimethyl ether (DME); volatile hydrocarbons such as n-butane, propane or isobutane; and mixtures thereof, optionally with at least one chlorohydrocarbon and/or fluorohydrocarbon including Freon™ and Dymel™. Carbon dioxide, nitrous oxide, nitrogen, or compressed air may also be used as the propellant. The anti-chafing composition and at least one propellant may be in the same compartment or in different compartments in the aerosol container. In one embodiment, the concentration of propellant generally ranges from 5% to 95% by pressurized weight and for example, from 50% to 85%, by weight relative to the total weight of the pressurized composition.

Preservative Compounds:

In one embodiment, the anti-chafing composition may also include at least one preservative compound in combination with the topical anti-chafing boron nitride material. In one embodiment, the preservative compound is present in an amount of 0.5% and about 3% by weight of the formulation. Desirably, the preservative compound is effective against yeast, particularly *Candida albicans*; molds, particularly *Aspergillus niger*; and bacteria, particularly *S. aureus, E. coli*, and *E. cloacae*. Examples include disodium ethylene diamine tetraacetic acid, methylparaben, and diazolidinyl urea. Disodium ethylene diamine tetraacetic acid also serves as a chelating agent to block the activity of bacterial ureases, lipases, proteases, and decarboxylases produced by *Klebsiella pneumoniae, Proteus mirabilus*, and *E. coli* bacteria amongst others. Other preservative compounds known to those skilled in the art may also be used.

Bacteriostatic/Bactericidal Agents:

In one embodiment, the anti-chafing composition may comprise at least one additional bacteriostatic agent and/or bactericidal agent such as 2,4,4'-trichloro-2'-hydroxydiphenyl ether (Triclosan), 2,4-dichloro-2'-hydroxydiphenyl ether, 3',4',5'-trichlorosalicylanilide, 1-(3',4'-dichlorophenyl)-3-(4'-chlorophenyl)urea (Triclocarban) and 3,7,11-trimethyl-dodeca-2,5,10-trienol (Farnesol); quaternary ammonium salts, for example, cetyltrimethylammonium salts and cetylpyridinium salts; chlorhexidine salts; diglyceryl monocaprate, diglyceryl monolaurate and glyceryl monolaurate; and polyhexamethylene biguanide salts.

Fragrances:

In one embodiment, the anti-chafing composition may also include fragrances. Examples include but are not limited to citrus, floral, spicy, lavender, woody, mossy, oriental, herbal, leather-tobacco, and aldehydic groups. Typically, fragrance materials are supplied as concentrates, which generally contain up to about 3 percent fragrance by weight. Examples include natural products such as essential oils, flower oils, natural extracts from resins, gums, balsams, beans, mosses and other plants, and animal products such as ambergris and musk, as well as synthetic aromatic materials.

Characteristics of the Composition of the Invention:

In one embodiment, the composition of the invention affords non-sticky, non-waxy in-use, cooling, and lubricious characteristics upon application onto the skin or a surface to be in contact with the skin. When applied onto a surface such as the skin, a piece of cloth, or a surface, the composition forms a thin, low residue film over the applied surface. The applied film remains substantially as such over extended periods of time after application, thus protecting the skin and providing the needed therapeutic anti-chafing properties. When applied as a stick, a lotion, a cream, or in powder form directly onto the skin, the anti-chafing composition suitably adheres to the skin and provides a good glide feel to the skin, while still retaining a good product stability.

In one embodiment, the composition is characterized as leaving a visible residue index of from 5 to about 100 L-value. In a second embodiment, the composition has a visible residue index of 10 to 80 L-value. In a third embodiment, the composition has an L-value of 30 to 50.

The term "visible residue index" as used herein refers generally to the extent to which the composition is visibly apparent as a thin topical film after application to the skin, and, more specifically, refers to visible residue values (expressed as an L-value on the L, a, b color scale). The L-value test is performed at 27° C., under atmospheric pressure, and at 15% relative humidity on a stick composition having a product hardness of about 500 gram-force to about 5,000 gram-force. In this test, a piece of black felt, approximately 10 cm×30 cm, is attached to a movable horizontal slide which is movably attached or fixed to a larger mechanical unit. An example of a suitable piece of black felt for use herein is Supreme Robe Velour, FN-6554, Color 404L, Style 31854, available from So-Fro Fabrics, Evendale, Ohio, U.S.A. An example of a suitable mechanical assembly for use herein is the Release and Adhesion Tester, Serial No. A-14934, manufactured by Testing Machines, Inc., Amityville, N.Y., U.S.A., or a Velmex Unislide Positioning System, Unislide assembly series (MB6000), available from Velmex, Inc., Bloomfield, N.Y., U.S.A. The anti-chafing stick composition contained within partially extends out about 0.5 cm from a conventional package or container, and is positioned perpendicular to and above the piece of felt, such that the product extends out of the package and faces the piece of felt. The surrounding package is positioned in place using a mechanical arm or other device suitable for applying the requisite movement to the product. The composition is then slowly moved toward and allowed to gently contact the attached piece of black felt. A 1,000 gram weight is placed on the product sample so that the product continuously contacts the piece of black felt during testing. The weighted sample is then moved repeatedly back and forth across the piece of felt at a fixed speed (about 3 cm/second), and with a fixed amount of applied pressure provided by the weighted product, until the about 1.75 grams of the stick composition is evenly applied over a 5 cm×20 cm area of the piece of black felt. The piece of felt is then carefully removed from the apparatus. A calibrated Minolta CR-300 chromameter (available from Minolta Corp., Ramsey, N.J., U.S.A.) is then used to measure the L-value (on the L, a, b color scale) with an average L-value determined for multiple measurements.

Applications of the Composition of the Invention:

The anti-chafing composition can take any form which is typical of dermatological products, for example, hot pour formulations, water-in-oil emulsions, oil-in-water emulsions, gels, sticks, sprays, anhydrous formulations, aerosol formulation, powder form, and the like.

In one embodiment, the anti-chafing composition is dispensed using a pump bottle for single-unit dosages, wherein the pump bottle is designed for sufficient individual (single-unit dosage) dispensing depending on the final application. In another embodiment, the anti-chafing composition is applied as single unit dosages in the form of a sheet, e.g., using an absorbent flexible substrate such as a non-woven cloth made from fibers or filaments. In one embodiment, the absorbent flexible substrate (e.g., in a sheet form) is soaked with an aqueous mixture of the anti-chafing composition. The resultant soaked sheet is pressed to remove any excess surfactant, and then dried, for single sheets having a sufficient amount of anti-chafing for single or individual applications.

In one embodiment, the composition of the invention may be used as a topical application to be applied directly to clothing/shoes, and/or to the skin, prior to the individual engaging in physical activities such as running, hiking, jogging, walking, etc. In a second embodiment, the composition is applied onto the skin of individuals afflicted with skin disorders such as burned skin, varicose ulcers, diabetic ulcers, diaper exanthema, etc., to provide soothing comfort to the skin. In a third embodiment, the formulation may be applied to patients with foot surgery, prior to or in connection with casts, to avoid peeling and callosities. In yet a fourth embodiment, the composition is applied onto a bandage or a gauze pad prior to applying onto the skin of burned patients, to provide comfort to the skin in the healing process.

In embodiments wherein the composition is applied as treatment for diaper rash, the composition is particularly suitable for the treatment of diaper rash caused by friction rash and/or intertrigo. Friction rash is the most common form of diaper rash, and affects almost all infants at some time. It is most common on areas where friction is most pronounced, such as the inner thighs, or under the elastic of diapers that are too tight. It comes and goes quickly, and responds well to frequent diaper changes, airing out, and protective barriers. Intertrigo is caused by moist heat, such as that which commonly occurs deep in skin folds.

For diaper rash treatment, the composition can be directly applied onto the infant's skin areas most inflicted by diaper rash problems, using an atomizing pump spray dispenser, if the composition is in an aqueous form, or a "pump dispenser" for a composition in a cream, lotion, or ointment form. In one embodiment of a solid anti-chafing composition, i.e., in the form of a wand or a stick, or a powder form, the composition is rubbed or rolled onto the skin areas of the infant often afflicted by diaper rash problems.

The invention is further illustrated by the following non-limiting examples:

Examples 1-5

Liquid Anti-Chafing Composition

Liquid Compositions are prepared having the ingredients and the amounts set out below. Each of these compositions is prepared by adding all of the ingredients to the cyclomethicone and mixing to form a homogeneous suspension.

| Ingredient in wt. % | Ex. 1 | Ex. 2 | Ex. 3 | Ex. 4 | Ex. 5 |
|---|---|---|---|---|---|
| Cyclomethicone (DC 344) | 74.5 | 73.5 | 66.90 | 60.50 | 59.85 |
| BN coated with polydimethylsiloxane | 21 | 22 | 28.6 | — | — |
| BN powder | — | — | — | 35 | 32.1 |
| Quaternium-18 hectorite | 3.5 | 3.5 | 3.5 | 3.5 | — |
| Propylene carbonate | 1 | 1 | 1 | 1 | — |
| Talc | — | — | — | — | 4.95 |
| Silica | — | — | — | — | 3.10 |

Examples 6-8

Aerosol Anti-Chafing Composition

Aerosol Compositions are prepared having the ingredients and the amounts set out below. Each of these compositions is prepared by adding all of the ingredients, except the propellant, to the cyclomethicone, and mixing to form a homogeneous suspension. The suspension is placed in an aerosol can and the propellant is added. In one embodiment, the propellant is a 1:2 blend of propellants 152A and A31.

| Ingredient in wt. % | Ex. 6 | Ex. 7 | Ex. 8 |
|---|---|---|---|
| Cyclomethicone (DC 344) | 24.6 | 26.13 | 23.13 |
| BN coated with polydimethylsiloxane | 13.18 | 11.65 | — |
| BN powder | — | — | 11.65 |
| Talc | 2.03 | 2.03 | 2.03 |
| Silica | 1.27 | 1.27 | 1.27 |
| Propellant | 58.92 | 58.92 | 58.92 |

Examples 9-12

Solid Stick Anti-Chafing Composition

Solid Stick compositions are prepared having the ingredients and the amounts set out below. Each of these compositions is prepared by mixing all of the ingredients, except the fragrance, with the cyclomethicone, heating the mixture to melt the gelling agents, and cooling the mixture to form a solid stick, with the fragrance being added during the cooling step and prior to solidification.

| Ingredient in wt. % | Ex. 9 | Ex. 10 | Ex. 11 | Ex. 12 |
|---|---|---|---|---|
| Cyclomethicone (DC 345) | 41.12 | 36.32 | 46.2 | 48.3 |
| BN powder, coated with polydimethylsiloxane | 26.18 | 30.98 | — | — |
| BN powder | — | — | 29.2 | 27.9 |
| Stearyl alcohol | 15.53 | 15.53 | 15.53 | 15.53 |
| PPG-10 butanediol | 4.8 | 4.8 | — | — |
| C12-C15 alcohols benzoate | 3.84 | 3.84 | — | — |

-continued

| Ingredient in wt. % | Ex. 9 | Ex. 10 | Ex. 11 | Ex. 12 |
|---|---|---|---|---|
| Hydrogenated castor oil | 2.84 | 2.84 | 3 | 3 |
| Myristyl myristate | 1.92 | 1.92 | 4 | — |
| PEG-8 distearate | 0.92 | 0.92 | — | 1 |
| Silica | — | — | 1.8 | 1.8 |
| Fragrance | 28.5 | 28.5 | 2.3 | 2.8 |

Example 13

Solid Block Anti-Chafing Composition Consisting Essentially of Boron Nitride

A mixture comprising 29.4 wt. % BN powder (grade AC6004 from GE Advanced Materials), 68.6 wt. % of another BN powder (grade AC6100 from GE Advanced Materials), and 2 wt. % of carbon black (grade N991 from Cancarb) is homogenously blended together. The blend is pressed into a billet in a uniaxial press. The block is then cut into a plurality of blocks. The block is then sintered for 10-30 hours at 1700-2300° C., forming low-density BN blocks, with density ranging from 0.20 to 1.5 g/cm3, and with a fairly high $O_2$ concentration of <1.0 wt %.

Examples 14-16

Cream Anti-Chafing Composition

Cream Compositions are prepared having the ingredients and the amounts set out below. Each of these compositions is prepared by adding all of the ingredients, except silica and fragrance, until uniform, heating to 50° C., then mixing under high shear agitation for twenty minutes. The mixture is passed through a Sonolator shear device to increase the viscosity. The fragrance is added last and is mixed until uniform.

| Ingredient in wt. % | Ex. 13 | Ex. 14 | Ex. 15 |
|---|---|---|---|
| Silicone latex (DC 2-9065) | 54.54 | 54.54 | 54.54 |
| Dimethicone (DC 225) | 10 | 10 | 9.31 |
| Cyclomethicone (DC 344) | 1.31 | 7.31 | — |
| BN powder, coated with polydimethylsiloxane | 31.5 | 25.5 | — |
| BN powder | — | — | 33.50 |
| Trihydroxystearin | 0.4 | 0.4 | 0.4 |
| Hydrated silica (Sylox 2) | 1 | 1 | 1 |
| Fragrance | 1.25 | 1.25 | 1.25 |

Example 17

Alternate Solid Stick Form

In another embodiment, the solid block can be formed at low temperatures by using an appropriate BN powder and a synthetic or natural wax, paraffin, non-ionic surfactant, etc. as a binder. The BN powder component at loading of 85 to 99.5 wt % is dry blended with the binder component (0.5 to 15 wt %) using a v-blender mixer, and the dry mixture is charged into a mold heated to 250° F. and pressed at a pressure of between 250 and 1500 psig, cooled to room temperature, and de-molded to form a bar or other desired shape.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

All citations referred herein are expressly incorporated herein by reference.

The invention claimed is:

1. An anti-chafing composition for maintaining and/or improving skin health in an area covered by an article, the composition comprising an aqueous dermatologically acceptable carrier and from 0.5 to 15 wt. % of boron nitride particles, containing boron nitride particles having a particle size of from about 10 to about 250 μm, wherein the composition, upon topical application onto skin, leaves a layer comprising a chafe-reducing effective amount of boron nitride particles on the skin.

2. The anti-chafing composition of claim 1, further comprising a dermatologically acceptable carrier selected from the group consisting of organic solutions, gels, an aerosols, emulsifiers, aqueous lotions, water-in-oil emulsions, oil-in-water emulsions, and surfactants.

3. The anti-chafing composition of claim 1, wherein the composition upon topical application on the skin, leaves a residual layer having an L-value index ranging from 5 to about 100.

4. The anti-chafing composition of claim 1, in the form of an aerosol, pump spray, liquid, roll-on, lotion, cream, gel, foam, powder, or stick.

5. The anti-chafing composition of claim 1, wherein the composition is topically dispensed on the skin using a pump bottle for single-unit dosages.

6. The anti-chafing composition of claim 1, wherein the composition is topically dispensed on the skin using an absorbent flexible substrate.

7. The anti-chafing composition of claim 1, comprising boron nitride having an aspect ratio from about 10 to about 300.

8. The anti-chafing composition of claim 1, comprising boron nitride having an oxygen content from 0.2 to 2.5 wt %.

9. The anti-chafing composition of claims 1, comprising boron nitride having a graphitization index of less than 7.

10. The anti-chafing composition of claims 1, where the dermatologically acceptable carrier comprises a volatile silicone or a non-volatile silicone.

11. An anti-chafing composition consisting essentially of boron nitride having an average particle size from about 10 to about 250 μm, wherein the composition has a density ranging from 0.20 to 1.500 $g/cm^3$, and an $O_2$ concentration ranging from 0.2 to 1.3 wt. %, wherein the composition, upon topical application onto skin, leaves a layer comprising a chafe-reducing effective amount of boron nitride particles on the skin.

12. The anti-chafing composition of claim 11, wherein the composition contains from 95 to 99.99 wt. % boron nitride and 0.01 to 5 wt. % carbon.

13. The anti-chafing composition of claim 1, wherein the boron nitride particles have a primary average particle size of less than 20 μm.

* * * * *